(12) United States Patent
Gläser et al.

(10) Patent No.: US 7,939,692 B2
(45) Date of Patent: May 10, 2011

(54) CATALYST AND PROCESS FOR PRODUCING KETONE USING THE SAME

(75) Inventors: Roger Gläser, Jena (DE); Sudhir Dapurkar, Sendai (JP); Carsten Stöcker, Meerbusch (DE); Junichi Nishimoto, Ibaraki (JP); Masayoshi Murakami, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/087,312

(22) PCT Filed: Jan. 3, 2007

(86) PCT No.: PCT/EP2007/000028
§ 371 (c)(1),
(2), (4) Date: Dec. 29, 2008

(87) PCT Pub. No.: WO2007/080067
PCT Pub. Date: Jul. 19, 2007

(65) Prior Publication Data
US 2009/0171123 A1    Jul. 2, 2009

(30) Foreign Application Priority Data

Jan. 11, 2006 (DE) .................. 10 2006 001 482

(51) Int. Cl.
*C07C 45/34* (2006.01)
(52) U.S. Cl. ......... 568/357; 568/360; 568/365; 568/376
(58) Field of Classification Search .................. 568/360, 568/357, 365, 376
See application file for complete search history.

(56) References Cited

U.S. PATENT DOCUMENTS

| | | | | |
|---|---|---|---|---|
| 4,853,357 A | * | 8/1989 | Vasilevskis et al. | 502/165 |
| 5,557,014 A | * | 9/1996 | Grate et al. | 568/401 |

FOREIGN PATENT DOCUMENTS

| | | |
|---|---|---|
| CA | 2 360 499 | 9/2000 |
| JP | 06-091170 | 4/1994 |
| JP | 11-226418 | 8/1999 |
| WO | WO 99/59718 | 11/1999 |
| WO | WO 2006/046852 A1 | 5/2006 |

OTHER PUBLICATIONS

Adam et al., "The Origin of the Positive Effect of Cadmium Acetate on the Action of Supported Palladium Catalysts," Chem. Eur. J., 1998, pp. 1458-1469, vol. 4, No. 8.
Beck et al., "A new family of mesoporous molecular sieves prepared with liquid crystal templates," J. Am. Chem. Soc., 1992, pp. 10834-10843, vol. 114, No. 27.
Boger et al., "Influence of the aluminum content on the adsorptive properties of MCM-41," Microporous Materials, 1997, pp. 79-91, vol. 8.
Brink et al. "Catalytic conversions in water. Part 10. Aerobic oxidation of terminal olefins to methyl ketones catalysed by water soluble palladium complexes," Chem. Commun., 1998, pp. 2359-2360.
Cornell et al., "Discovery of and Mechanistic Insight into a Ligand-Modulated Palladium-Catalyzed Wacker Oxidation of Styrenes Using TBHP," J. Am. Chem. Soc., 2005, pp. 2796-2797, vol. 127., No. 9.
Cornils et al. "Applied Homogeneous Catalysis with Organometallic Compounds," A Comprehensive Handbook in Two Volumes, VCH, 1996, pp. 374-393, vol. 1.
Diaz et al., "Cyclohexene reactivity over palladium acetate supported in liquid phase," Catalysis Letters, Jul. 2004, pp. 169-175, vol. 96, Nos. 3-4.
Espeel et al., "Palladium-Copper-exchanged Y Type Zeolites: A True Heterogeneous Wacker Catalyst," J. Chem. Soc., Chem. Commun., 1991, pp. 669-671, No. 10.
Henry P., V.3 "Palladium-Catalyzed Reactions Involving Nucleophilic Attack on π-Ligands of Palladium-Alkene, Palladium-Alkyne, and Related Derivatives" through V.3.1.1, Handbook of Organopalladium Chemistry for Organic Synthesis, 2002, pp. 2119-2139.
Kim et al., "A modified Wacker catalysis using heteropolyacid: Interaction of heteropolyanion with Cu(II) in cyclohexene oxidation," Applied Catalysis A: General, 1997, pp. 15-26, vol. 155.
Kishi et al., "Wacker-type oxidation of cyclopentene under dioxygen atmosphere catalyzed by Pd(OAc)$_2$/NPMoV on activated carbon," Tetrahedron Letters, 2000, pp. 99-102, vol. 41.
Liu et al., "Direct oxidation of benzene to phenol by molecular oxygen over catalytic systems containing Pd(OAc)$_2$ and heteropolyacid immobilized on HMS or PIM," J. Mol. Catalysis A: Chemical, 2006, pp. 247-255, vol. 256.
Melgo et al., "Wacker oxidation of cyclohexene in the presence of Pd(NO$_3$)$_2$/CuSO$_4$/H$_3$PMo$_{12}$O$_{40}$," Applied Catalysis A: General, 2004, pp. 217-221, vol. 273.
Miller et al., "Improved method for the Wacker oxidation of cyclic and internal olefins," J. Org. Chem., 1990, pp. 2924-2927, vol. 55, No. 9.
Mitsudome et al., "Highly efficient Wacker oxidation catalyzed by heterogeneous Pd montmorillonite under acid-free conditions," Tetrahedron Letters, 2006, pp. 1425-1428, vol. 47.
Moiseev et al., "Allylic oxidation of alkenes with palladium catalysts," Coordination Chem. Reviews, 2004, pp. 2381-2391, vol. 248.
Nagahara et al., "Partial hydrogenation of benzene to cyclohexane," Applied Surface Science, 1997, pp. 448-451, vol. 121/122.
Nishimura et al., "Palladium(II)-catalyzed oxidation of terminal alkenes to methyl ketones using molecular oxygen," J. Chem. Soc., Perkin Trans. 1, 2000, pp. 1915-1918.

(Continued)

*Primary Examiner* — Sikarl A Witherspoon
(74) *Attorney, Agent, or Firm* — Foley & Lardner LLP

(57) ABSTRACT

There are disclosed a method for producing a ketone compound, which comprises reacting an olefin compound with molecular oxygen and water in the presence of an effective amount of proton and a catalyst containing i) a chlorine-free palladium source, ii) a heteropoly acid or an acid salt of a heteropoly acid, and iii) a mesoporous silicate, and catalysts for the process.

7 Claims, No Drawings

OTHER PUBLICATIONS

Nowinska et al., "Heteropoly compounds incorporated into mesoporous material structure," Applied Catalysis A: General, 2003, pp. 115-123, vol. 256.

Ogawa et al., "Liquid Phase Oxidation of Cyclo-olefins by a $PdSO_4$-Heteropolyacid Catalyst System," J.C.S. Chem. Comm., 1981, pp. 1274-1275.

Ogawa et al., "Palladium (II) Sulfate-Heteropoly Acid-catalyzed Oxidatino of Cycloolefins in Liquid Phase," Bull. Chem. Soc. Jpn., 1984, pp. 1908-1913, vol. 57, No. 7.

Passoni et al., "Heterogenization of $H_6PMo_9V_3O_{40}$ and palladium acetate in VPI-5 and MCM-41 and their use in the catalytic oxidation of benzene to phenol," J. Mol. Catalysis A: Chemical, 1998, pp. 229-235, vol. 134.

Schuchardt et al., "Cyclohexane oxidation continues to be a challenge," Applied Catalysis A: General, 2001, pp. 1-17-vol. 211.

Soeda et al., "Wacker-Type Oxidation of Cyclohexene over Palladium-Supported Heteropoly Compounds," Chem. Soc. Jpn., 1993, pp. 917-923, No. 8.

Stobbe-Kreemers et al., "Heteropolyanions as Redox Components in Heterogeneous Wacker Oxidation Catalysts." 1995, pp. 175-186, Academic Press, Inc.

Stobbe-Kreemers et al., "Palladium Salts of Heteropolyacids as Catalysts in the Wacker Oxidation of 1-Butene," J. Catalysis, 1995, pp. 187-193, vol. 154.

Stobbe-Kreemers et al., "Palladium salts of heteropolyanions as catalysts in heterogeneous Wacker oxidation of 1-butene," J. Mol. Catalysis A: Chemical, 1996, pp. 247-253, vol. 107.

Tsuji J., "Palladium Reagents and Catalysts," New Perspectives for the 21st Century, 2004, pp. 32-35, John Wiley & Sons, Ltd., England.

Verhoef et al., "A study on the stability of MCM-41-supported heteropoly acids under liquid- and gas-phase esterification conditions," Microporous and Mesoporous Materials, 1999, pp. 365-371, vol. 27.

Yokota et al., "Molybdovanadophosphate (NPMoV)/hydroquinone/ $O_2$ system as an efficient reoxidation system in palladium-catalyzed oxidation of alkenes," J. Mol. Catalysis A: Chemical, 1996, pp. 113-122, vol. 114.

Yokota et al., "Selective Wacker-type oxidation of terminal alkenes and dienes using the Pd(II)/molybdovanadophosphate (NPMoV)/$O_2$ system," Tetrahedron Letters, 2002, pp. 8887-8891, vol. 43.

Zweni et al., "Dendrimer-Palladium Complex Catalyzed Oxidation of Terminal Alkenes to Methyl Ketones," Adv. Synth. Catal., 2004, pp. 849-854, vol. 346.

\* cited by examiner

CATALYST AND PROCESS FOR PRODUCING KETONE USING THE SAME

FIELD OF THE INVENTION

The present invention relates to a catalyst which can be used for oxidizing an olefin with air or molecular oxygen to produce a corresponding ketone.

Ishii et al. reported Wacker-type oxidation of cyclopentene under oxygen atmosphere catalyzed by $Pd(OAc)_2$/NPMoV on activated carbon (Tetrahedron Letters 41 (2000) 99-102). The carbon supported catalyst has not always been efficient. It is disclosed that an oxidation catalyst containing $H_6PMo_9V_3O_{40}$ encapsulated into MCM-41 and palladium acetate can be used as a catalyst for oxidation of benzene into phenol with molecular oxygen (Journal of Molecular Catalysis A: Chemical 134(1998)229-235).

According to the present invention, the oxidation of an olefin to a ketone can be carried out efficiently and selectively in the presence of a catalyst of the invention.

The present invention relates to
a catalyst comprising
a) a chlorine-free palladium source, an acid salt of a heteropoly acid, and a mesoporous silicate, or
b) a chlorine-free palladium source, a heteropoly acid, and a mesoporous silicate, provided that in option b) the catalyst is not a catalyst comprising palladium acetate and $H_6PMo_9V_3O_{40}$ encapsulated into MCM-41.

The invention further relates to method for producing a ketone compound, which comprises reacting an olefin compound with molecular oxygen and water in the presence of an effective amount of proton and a catalyst comprising
i) a chlorine-free palladium source, ii) a heteropoly acid or an acid salt of a heteropoly acid, and iii) a mesoporous silicate.

The chlorine-free palladium source that may be used in the present invention includes, for example, palladium metal, a chlorine-free palladium compound and mixtures thereof.

The chlorine-free palladium salt herein means that the palladium source itself is not a chlorine salt.

Examples of the chlorine-free palladium compounds include for example, a chlorine-free salt of palladium such as an organic acid salt of palladium, an oxyacid salt of palladium, palladium oxide, palladium sulfide, organic or inorganic complexes of the salts, oxides, and sulfides, and mixtures thereof.

Examples of the organic acid salt of palladium include, for example, palladium acetate and palladium cyanide.

Examples of the oxyacid salt of palladium include, for example, palladium nitrate and palladium sulfate.

Examples of the organic or inorganic complexes of the salts, oxides, and sulfides include, for example, tetraamminepalladium(II) nitrate, bis(acetylacetonato) palladium and the like.

Preferred is the organic acid salt of palladium or oxyacid salt of palladium. More preferred is palladium acetate.

The heteropoly acid or acid salt of a heteropoly acid that may be used in the present invention is not specifically limited. The heteropoly acid herein means a condensation product of an oxyacid containing 2 or more central ions. For example, a heteropoly acid is composed of the oxyacid ion of elements such as P, As, B, Sn, Si, Ti or Zr (e.g., phosphoric acid, silicic acid, boric acid and the like) and the oxyacid ion of elements such as V, Mo or W (e.g., vanadic acid, molybdic acid, tungstic acid and the like). The heteropoly acids encompass those that can be synthesized from combinations of the oxyacids.

Preferred heteropoly acids or acid salts of heteropoly acids are those containing at least one element selected from the group consisting of P, Si, V, Mo and W, and more preferred heteropoly acids or acid salts of the heteropoly acids are those containing at least one element selected from the group consisting of P, V, Mo and W.

The still more preferred heteropoly acid or acid salt of a heteropoly acid is a heteropoly acid or an acid salt of a heteropoly acid containing at least P and V both, as its composing elements, or a heteropoly acid or an acid salt of a heteropoly acid containing at least Mo or V or both Mo and V Typical examples of the heteropoly anions of the heteropoly acid or acid salt of a heteropoly acid are as follows:
$XM_{12}O_{40}$, $XM_{10}O_{34}$, $XM_{12}O_{42}$, $XM_{11}O_{39}$, $XM_{10}O_m$, $XM_9O_{32}$, $XM_6O_{24}$, $X_2M_{18}O_{62}$, $X_2M_{18}O_{56}$, $X_2M_{12}O_{42}$, $X_2M_{17}O_m$, and $XM_6O_m$,
wherein X is a central atom and is preferably B, Si, or P, M represents a transition metal or metals, and is preferably Mo, W, or V, and m indicates an integer of 15 to 80.

Among the average composition formulae of the heteropoly anion, preferred is the average composition formula (1A):

$$XM_{12}O_{40} \tag{1A}$$

wherein X is Si or P, and M represents at least one element selected from the group consisting of Mo, V and W, or
a hereropoly acid of an average composition formula (1B):

$$X_2M_{18}O_{62} \tag{1B}$$

wherein X is Si or P, and M represents at least one element selected from the group consisting of Mo, V and W.

Examples of the heteropoly anion having such a composition include, for example, the anions of phosphomolybdic acid, phosphotungstic acid, silicomolybdic acid, silocotungstic acid, phosphomolybdotungstic acid and phosphovanadomolybdic acid. The anion of phosphovanadomolybdic acid, phosphomolybidic acid or phosphomolybdotungstic acid is the particularly preferred heteropoly anion.

Preferred heteropoly acids are
phosphovanadomolybdic acid of formula (2A):

$$H_{3+n}[PV_nMo_{12-n}O_{40}] \tag{2A}$$

wherein n is an integer of 1 to 11, more preferably n is an integer of 1 to 8, and is still more preferably 2 to 8, yet still more preferably 4 to 8;
phosphovanadotungstic acid of formula (2B)

$$H_{3+n}[PV_nW_{12-n}O_{40}] \tag{2B}$$

wherein n is an integer of 1 to 11, more preferably n is 1 to 8, and still more preferably 4 to 8;
phosphomolybdotungstic acid of formula (2C):

$$H_3[PMo_{12-n}W_nO_{40}] \tag{2C}$$

wherein n is an integer of 0 to 12, preferably an integer of 0 to 10, more preferably an integer of 1 to 6; and
phosphomolybdotungstic acid of formula (2D)

$$H_6[P_2Mo_{18-n}W_nO_{62}] \tag{2D}$$

wherein n is an integer of 0 to 18, more preferably n is 0 to 10, and still more preferably 0 to 6.

Preferred acid salts of a heteropoly acid are an acid salt of phosphovanadomolybdic acid of formula (3A):

$$A_{3+n}[PV_nMo_{12-n}O_{40}] \tag{3A}$$

wherein A represents a cationic moiety consisting of proton(s) and cation(s) other than proton, in a balancing proportion, and n is an integer of 1 to 11;

an acid salt of phosphovanadotungustate of formula (3B):

$$A_{3+n}[PV_nW_{12-n}O_{40}] \quad (3B)$$

wherein A represents a cationic moiety consisting of proton(s) and cation(s) other than proton, in a balancing proportion, and n is an integer of 1 to 11, more preferably n is 1 to 8, and still more preferably 4 to 8;

an acid salt of phosphomolybdotungstate of formula (3C):

$$A_3[PMo_{12-n}W_nO_{40}] \quad (3C)$$

wherein A represents a cationic moiety consisting of proton(s) and cation(s) other than proton, in a balancing proportion, and n is an integer of 0 to 12, preferably an integer of 0 to 10, more preferably an integer of 1 to 6; and an acid salt of phosphomolybdotungstate of formula (3D):

$$A_6[P_2Mo_{18-n}W_nO_{62}] \quad (3D)$$

wherein A represents a cationic moiety consisting of proton(s) and cation(s) other than proton, in a balancing proportion, and n is an integer of 0 to 18, more preferably n is 0 to 10, and still more preferably 0 to 6.

Examples of the cation include, for example, ammonium including tertiary ammonium salt such as cetyltrimethylammonium bromide, cetylpyridinium chloride or the like, an alkali metal (e.g., sodium, potassium, cesium, lithium and the like), an alkaline earth metal (e.g., barium, magnesium, calcium, and the like) and mixtures thereof.

The acid salt of a heteropoly acid of the invention typically has, for example, hydrogen atom(s) and $NH_4$ in the cationic moiety in a balancing manner. The acid salt of a heteropoly acid is typically produced by substitution of hydrogen atom or atoms with other cation(s). The proportion of $NH_4$ to H, designated as $NH_4/H$, is preferably 0.1 to 10, more preferably 0.2 to 8 and further more preferably about 0.3 to about 5. In addition, n in the formula (3) is preferably 1 to 8 and more preferably 4 to 8. The acid salt of a heteropoly acid may be used alone or as mixtures thereof.

The amount of the acid salt of a heteropoly acid, or the heteropoly acid that may be used depends upon the kind of the acid salt of a heteropoly acid or the heteropoly acid, and the kind and concentration of the olefin to be reacted.

The acid salt of a heteropoly acid, or the heteropoly acid is usually used in the amount of 0.001 mole or more, preferably 0.005 mole or more, yet more preferably 0.01 mole or more, still further more preferably 0.05 mole or more per mol of palladium, and the upper limit thereof is usually 500 moles, preferably 100 moles, yet more preferably 10 moles, still further more preferably 1 mole per mol of palladium.

The mesoporous silicate in this specification means that the mesoporous silicate has ordered mesopores the diameter of which is 2 nm to 50 nm.

The framework type codes of the mesoporous silicate are based on the definition of IZA (International Zeolite Association). Studies in Surface Science and Catalysis 148 (2004) 53 can be referenced with respect to M41S(MCM) types.

Examples of the mesoporous silicate include, for example, mesoporous silica, which is consisting of silica, and metallo-silicates containing at least one element selected from the group consisting of Al, Ti, Zr, Ga, Fe, B, V, Nb, Cr, Mo, Mn, Co and Sn in its framework.

Examples of the mesoporous silicate include, MCM-41, MCM-48, SBA-types such as SBA-15 or SBA-16(D. Zhao, et al., Science 279 (1998)548; Zhao et al., J. Am. Chem. Soc. 120 (1998) 6024), and HMS (hexagonal mesoporous silicate), which are mesoporous silicates having mesopores the diameter of which is 2 nm to 50 nm.

The mesoporous silicate is typically synthesized by hydrolysis of silicic alkoxide such as tetraethylortho silicate in the presence of a template such as quaternary ammonium salts (e.g., dodecyltrimethylammonium chloride and cetyltrimethylammonium bromide (U.S. Pat. No. 5,098,684, Zeolite, 18, 408 to 416 (1997)), primary amines (e.g., n-dodecylamine (Science Vol. 267, 865), or a block copolymer (Science Vol. 269, 1242).

The mesoporous silicate such as siliceous MCM-41 may be prepared according to Beck et al., Nature 359, 710 (1992). Preparation of HMS may be carried out by a method according to Peter T. Tanev et al., (Science, vol. 267, p. 865). In addition, it can be synthesized by using silica such as precipitated silica and colloidal silica and sodium silicate such as liquid glass as a silicon source, for example, by hydrothermal synthesis, and then removing the template by washing with a suitable solvent such as toluene, methanol or acetone, or by calcination at a temperature of about 300° C. to 800° C., or by washing followed by calcination.

Among these mesoporous silicates, those having a larger surface area per unit weight are more preferably used. Preferred are those having a surface area of 200 $m^2$ to 2000 $m^2$ per 1 g of the mesoporous silicate and more preferred are those having 400 $m^2$ to 2000 $m^2$ per 1 g of the mesoporous silicate.

The shape of the fine pores and the sequential regularity are not specifically limited as long as there mesopores as defined above exist. The mesoporous silicates may be molded into a pellet shape, spherical shape, cylindrical shape and the like, if necessary, before or after contacting with a palladium compound and the heteropoly acid or an acid salt thereof.

The palladium compound, the heteropoly acid or the acid salt thereof, and the mesoporous silicate can be independently added to the reaction. The preparation of the catalyst of the invention is explained below with respect to the acid salt of a heteropoly acid as the catalyst component. The preparation of the catalyst of the invention can also be carried out using the heteropoly acid as the catalyst component in place of the acid salt of a heteropoly acid in the following procedures.

For example, the palladium compound, or the acid salt of a heteropoly acid is contacted with the mesoporous silicate, and the remaining component is separately added to the reaction.

Alternatively the palladium compound and the acid salt of a heteropoly acid are contacted with the mesoporous silicate in order or simultaneously to form a supported catalyst, which comprises a) the palladium compound and b) the acid salt of a heteropoly acid, wherein both components a) and b) are supported on the mesoporous silicate.

The catalyst of the present invention is typically produced by impregnation using a solution or suspension of the palladium compound or of the acid salt of a heteropoly acid or of both onto the mesoporous silicate.

For example, a solution of the palladium compound or of the acid salt of a heteropoly acid in a suitable solvent is prepared and the mesoporous silicate is added thereto, and then the resulting mixture is stirred to contact the components, during or after which a remaining component of the catalyst is added thereto, and the components are contacted each other to obtain a mixture. The mixture is usually filtered or evaporated to give the catalyst of the invention as a solid material, which may be further dried, if necessary.

Alternatively, a solution or suspension of the palladium compound and the acid salt of a heteropoly acid in a suitable solvent is prepared and the resulting mixture is contacted with the mesoporous silicate, and the mixture is subjected to similar treatment such as filtration, evaporation, or drying as above.

Examples of the suitable solvents that can dissolve the palladium compound or the acid salt of a heteropoly acid include, for example, water, alcohols (such as methanol or ethanol), and ketones (such as acetone), and nitrile (such as acetonitrile) or the like.

The amount of the palladium compound supported on the mesoporous silicate varies depending on the support and its amount, and is usually 0.001 to 40% by weight, preferably 0.01 to 30% by weight and more preferably 0.1 to 20% by weight of the mesoporous silicate.

The olefin compound that may be used in the present method is typically a substituted or unsubstituted cycloolefin.

Examples of the substituents include, for example, a halogen atom (e.g., chlorine, fluorine, bromine, and iodine), a hydroxyl group, a carboxyl group, a cyano group, an acyl group, a nitro group, an amino group, a cycloalkyl group, an aryl group, a heterocyclic ring group and the like.

Examples of the unsubstituted cycloolefin include, for example, a cycloolefin having about 4 to 20 carbons such as cyclobutene, cyclopentene, cyclohexene, cycloheptene, cyclooctene, cyclodecene, cyclododecene, cyclooctadecene, or the like.

A suitably employed cycloolefin is cyclohexene and cyclohexanone is produced therefrom efficiently.

Pure oxygen gas or air can be used or these gases may be used as gases containing molecular oxygen by dilution with an inert gas such as nitrogen or helium. The amount of the molecular oxygen that may be used is suitably adjusted depending on the kind and amount of the olefin compound to be oxidized, the solubility of oxygen in a solvent used and the like. Molecular oxygen is usually employed in the amount of 1 mol to about 100 moles per 1 mol of the olefin compound, preferably about 2 to about 50 moles and more preferably about 5 to about 20 moles. Partial pressure of molecular oxygen is preferably in the range of 0.01~10 MPa, more preferably 0.05~5 MPa.

The amount of water is typically 1 to 5000 moles per 1 mol of the olefin compound, preferably about 5 to about 1000 moles and more preferably about 10 to about 200 moles.

An inert organic solvent may be used in the oxidation reaction of the invention. Examples of the inert solvent include, for example, a polar organic solvent such as nitrile compounds (e.g., acetonitrile, propionitrile, benzonitrile and the like) or alcohols (e.g., methanol, ethanol, isopropanol and the like). The polar organic solvent is preferably used, and more preferred is acetonitrile. These solvents may be used alone or as mixtures thereof.

The effective amount of proton for the oxidation reaction may be provided by the heteropoly acid, or may be added to the oxidation reaction as a protonic acid. For example, protonic acids such as inorganic acids, organic acids, or mixtures thereof, which may be liquid or solid, may be added for the oxidation reaction.

Examples of the inorganic acid include, for example, sulfuric acid, nitric acid, hydrochloric acid, phosphoric acid, boric acid and the like.

Examples of the organic acids include, for example, carboxylic acids, and sulfonic acids both of which may have a halogen atom or atoms on their organic residues.

Examples of the carboxylic acids include, for example, formic acid, aliphatic carboxylic acids (such as acetic acid), alicyclic carboxylic acids (such as cyclohexanecarboxylic acid), aromatic carboxylic acids (such as benzoic acid), and the like.

Sulfonic acids include, for example, alkylsulfonic acids (such as methanesulfonic acid or ethanesulfonic acid), arylsulfonic acids (such as benzenesulfonic acid, p-toluenesulfonic acid or naphthalenesulfonic acid), and the like.

Examples of the solid protonic acids also include, for example, ion exchange resins such as sulfonic acid type ion exchange resins or the like, acidic zeolites and the like, and sulfated zirconia.

The amount of the protonic acid that may be used varies depending on the olefin compound to be oxidized, and the amount and kind of the solvent(s) used. For example, when the reaction is conducted in a liquid phase, which is a biphasic system comprising aqueous and organic phases, the protonic acid may be added so that the concentration of proton in the aqueous phase is preferably $10^{-5}$~10 mol/l, more preferably $10^{-3}$~1 mol/l. When the reaction is conducted in a uniform liquid phase formed from water and the organic solvent the acid may be added so that the concentration of proton in the uniform liquid phase is preferably $10^{-5}$~10 mol/l, more preferably $10^{-3}$~1 mol/l, assuming that the proton(s) of the protonic acid is totally liberated. The heteropoly acid as the component of the catalyst of the invention can also be a proton source in the reaction, and therefore the effective amount of proton as above can be provided solely from the catalyst of the invention.

The oxidation reaction is usually conducted in a temperature range of 0 to 200° C., preferably 10 to 150° C. and more preferably 30 to 100° C.

The reaction is usually conducted within a pressure range of 0.01 to 10 MPa (absolute pressure), preferably in a range of 0.05 to 7 MPa (absolute pressure) and more preferably in a range of 0.1 MPa to 5 MPa (absolute pressure).

The reaction solution or reaction gas that contains the reaction products is withdrawn or collected to isolate the desired ketones. The produced ketone compounds are typically separated by distillation, phase separation or the like.

Examples of the ketones include, for example, cyclopentanone, cyclohexanone, cyclododecanone and the like.

The reaction can be conducted in a batch-wise, semi-batch-wise, continuous method, or a combination thereof.

The catalyst may be used in a slurry method or a fixed-bed method.

The present invention will be further illustrated through Examples but it is not to be construed to limit the invention thereto.

EXAMPLES

Example 1

Preparation of Catalyst A

1. Molybdovanadophosphate (NPMoV):

A solution of $Na_2MoO_4.2H_2O$ (8.22 g, 34 mmol) in water (12 ml) was added to a solution of $NaVO_3$ (7.32 g, 60 mmol) in water (38 ml). To the resulting solution was added 85 wt.-% $H_3PO_4$ (7.6 g, 66 mmol) in water (10 ml) and the mixture was heated to 368 K under stirring for 1 h. After cooling of the mixture to 273 K, a saturated aqueous ammonium chloride solution (150 ml) was added to give NPMoV as a brown precipitate. The solid product was purified by recrystallization from water. It was then isolated by filtration and dried at about 363 K. The resulting NPMoV was a complex mixture of molybdovanadophosphate partly substituted by ammonium cations with an average atomic ratio of N/P/Mo/V=9.1/1.0/4.2/7.5. The average composition of the NPMoV may be represented by $(NH_4)_9H_2PMo_4V_{7.5}O_{40}.n\,H_2O$.

2. 10 wt.-% Pd (OAc)₂ 15 wt.-% NPMoV/MCM-41:

Pd(OAc)₂ (0.10 g) was dissolved in acetone (10 ml). Siliceous MCM-41 prepared as below was added to this solution. After stirring at room temperature for 2 h, NPMoV (0.15 g) was added, and the resulting mixture was stirred for 3-5 h at room temperature. The mixture was dried at 353 K to give [10 wt-% Pd(OAc)₂-15 wt-% NPMoV/MCM-41] in almost quantitative yield.

Synthesis of MCM-41 Used in Example 1:

8.13 g of sodium metasilicate (Fluka; Na₂O=51 wt.-%, SiO₂=48 wt.-%, H₂O=1 wt.-%) was added to 120 g of distilled water (referred to as a 'solution-X') and stirred for 30 min. Simultaneously, 'solution-Y' was prepared by mixing 4.48 g of tetradecyltrimethylammonuim bromide (TDT-MABr, Fluka; ≧98%) in 30 g of distilled water with 10 g of ethanol (Brüggemann; ca. 96%) and stirred for about 30 min. Then, both 'solution-X' and 'solution-Y' were mixed to get a clear gel. The pH of the gel was adjusted to approximately 11.5 by addition of 25-30 ml of 2NH₂SO₄. Finally, the resulting gel was transferred into polytetrafluoroethylene-lined stainless steel autoclaves (ca. 300 ml), which were kept in an air oven at 150° C. for 20 h. The solid product obtained, designated as as-synthesized MCM-41, was filtered off, washed with distilled water and dried at 80° C. for 12 h. The as-synthesized sample was then calcined at 550° C. (heating rate of 1° C. min⁻¹) for 2 h in N₂ with a flow rate of 50 ml min⁻¹ followed by 6 h in air (same flow rate)

(2) Synthesis of MCM-41 Used in Examples 2-35

Siliceous MCM-41 was prepared according to the literature (Carvalho et al., Zeolites, 18, 408, 1997) using sodium metasilicate (Na₂SiO₃) and Aerosil 200(Registered Trade Mark of NIHON Aerosil Company, Ltd.) with a molar ratio Na₂SiO₃/SiO₂ of 0.124:1 as silica source. Tetramethylammonium hydroxide (TMAOH) was used as a mineralizer and cetyltrimethylammonium bromide was used (CTMABr) as a template.

The reaction gel was prepared by suspending 6.3 g Na₂SiO₃ and 25 g Aerosil 200 in 13.12 g TMAOH (26%) and combining this suspension with 35.79 g CTMABr dissolved in 1043 g water into a stainless steel autoclave (1000 ml). It was heated to 105° C. with a heating rate of 17.5 K/h) and kept at that temperature for 48 hours. The obtained solid was separated by filtration, washed with water, dried at 80° C. in vacuo for 3 hours, and finally calcined at 530° C. for 1 hour under a flow of nitrogen and subsequently at the same temperature for 5 hours under a flow of air.

Synthesis of HMS 15.8 g of dodecylamine, 126.3 g of ethanol and 159.9 g of ion-exchange water were mixed, and 65.8 g of tetraethyl orthosilicate were added thereto. The resulting mixture was stirred for 18 hours at room temperature, and then filtered and washed to give an HMS precursor, which was then calcined for 1 hour under nitrogen atmosphere at 530° C. and further calcined in air for 5 hours at the same temperature to give the desired HMS.

Example 2

Cyclohexene Oxidation to Cyclohexanone with Air Over Catalyst A.

A mixture of 2 mmol of cyclohexene, acetonitrile/water (4.5 ml/0.5 ml), 38 mg of p-toluenesulfonic acid and 100 mg of Catalyst A were charged in a glass tube, and inserted into an autoclave having a capacity of 450 mL, and reacted under 2 MPa of pressurized air at 323 K for 6 hours to give cyclohexanone. Conversion of cyclohexene:96.7%, selectivity for cyclohexanone: 94.0%.

Example 3

The oxidation reaction was conducted in a similar manner as in Example 2 except that 8 mg of 96 wt.-% sulfuric acid was employed instead of p-toluenesulfonic acid (PTS) and nitrogen gas was introduced (3 MPa) in addition to the 2 MPa of pressurized air and acetonitrile/water (4.3 ml/0.7 ml) was used in place of acetonitrile/water (4.5 ml/0.5 ml) and an autoclave having a capacity of 120 ml was used.

Examples 4 and 7

In Examples 4 and 7, the reaction was conducted in a similar manner as in Example 3 except that HMS was used in place of MCM-41 and each reaction was conducted for the specified period of time shown in Table 1 below.

Example 5

The reaction was carried out under similar conditions as in Example 2 except that the reaction time was changed to 2 hours and an autoclave having a capacity of 120 ml was used. The results are shown in Table 1.

Example 6

The reaction was carried out under similar conditions as in Example 3 except that the reaction time was changed to 2 hours.

Example 8

A catalyst was prepared in a similar manner as in Example 1 except that 0.15 g of $H_7PV_4Mo_8O_{40}$ (manufactured by NIPPON INORGANIC COLOUR & CHEMICAL CO., LTD) was used in place of NPMoV.

Pd(OAc)₂ (0.1 g) was dissolved in acetone (10 ml) and then MCM-41 (1.0 g) was added to the solution. While stirring at room temperature, acetone (0.1 ml) solution of $H_{11}PV_4Mo_8O_{40}\cdot nH_2O$ (0.15 g) was added, and the suspension was continued stirring for 1 hour at room temperature. After evaporating the solvent at 1.4×10⁴ Pa (100 Torr), the resulting solid was dried in vacuo at 60° C. to give 10 wt.-% Pd(OAc)₂-15 wt.-% $HPV_4Mo_8O_{40}\cdot nH_2O$ /MCM-41. The oxidation reaction of cyclohexene was conducted in a similar manner as in Example 6.

Example 9

The reaction was carried out in a similar manner as in Example 8 except that $HPMo_6W_6O_{40}\cdot nH_2O$ was used in place of $HPV_4Mo_8O_{40}$.

Comparative Example

A mixture of 2 mmol of cyclohexene, acetonitrile/water (4.3 ml/0.7 ml), 8 mg of sulfuric acid, 8 mg of Pd(OAc)₂ and 17.3 mg of $HPMo_6W_6$ were charged in a glass tube, and inserted into an autoclave having a capacity of 120 mL, and reacted under air (2 MPa) and N₂ (3 MPa) and at 323 K for 2 hours to give cyclohexanone.

The results are shown in Table 1.

TABLE 1

| Example | Mesoporous silicate | Acid | Reaction time(hr) | Conversion of CHEN (%) | Selectivity for AN (%) |
|---|---|---|---|---|---|
| 2 | MCM-41 | PTS | 6 | 96.7 | 94 |
| 3 | MCM-41 | Sulfuric acid | 6 | 84 | 88 |
| 4 | HMS | Sulfuric acid | 6 | 79 | 88 |
| 5 | MCM-41 | PTS | 2 | 60 | 92 |
| 6 | MCM-41 | Sulfuric acid | 2 | 59 | 91 |
| 7 | HMS | Sulfuric acid | 2 | 55 | 88 |
| 8 | MCM-41 | Sulfuric acid | 2 | 68 | 89 |
| 9 | MCM-41 | Sulfuric acid | 2 | 38 | 90 |
| Comparative Example | none | Sulfuric acid | 2 | 30 | 85 |

CHEN: cyclohexene, AN: cyclohexanone

Example 10

$Pd(OAc)_2$ supported on MCM-41 was prepared in a similar manner as in Example 8 except that heteropoly acid was not used but the heteropoly acid was added to the reaction separately in the prescribed amount in Table 2.

Example 11

The reaction was carried out in a similar manner as in Example 10 except that MCM-41, heteropoly acid, and $Pd(OAc)_2$ (8 mg) were separately added to the reaction.

Examples 12, 13, and 17-33

The reaction was carried out in a similar manner as in Example 10 using each heteropoly acid as noted in Table 2.

Examples 14-16

The reaction was carried out in a similar manner as in Example 10 except that the prescribed amount of heteropoly acid as noted in Table 2 was used and 4 mmol of cyclohexene, which was twice as much as used in other Examples, was used.

Example 34

The reaction was carried out in a similar manner as in Example 11 except that sulfuric acid was not used.
Heteropoly Acid Heteropoly acid purchased from Nippon Inorganic Colour & Chemical Co., Ltd. was used except in Example 33.

Dawson-type heteropoly acid was prepared as follows and used in Example 33.
Preparation of Dawson-Type HPA, $H_6P_2Mo_{18}O_{62}$ Dawson-type HPA, $H_6P_2Mo_{18}O_{62}$ was prepared according to the literature (J. Biol. Chem., 189, 43 (1920) and U.S. Pat. No. 6,060,419). 6.7 g of $Na_2MoO_4 \cdot 2H_2O$ were dissolved in 30 ml of deionized water; 1 ml of 85% $H_3PO_4$ was added, followed by 5.3 ml of concentrated HCl. The contents were refluxed for 8 hours; then cooled to room temperature.

6.7 g of $NH_4Cl$ was added to the above solution, stirred for 10 minutes and the resulting yellow precipitate was collected by filtration under suction so that the collected solid is as dry as possible. The collected solid was redissolved in an equal weight of deionized water and refiltered to remove any insoluble material. $NH_4Cl$ was added in the filtrate to make a 20% solution. After standing for 8 hours, the solid was filtered under suction as dry as possible and redissolved in just enough deionized water. The solution was evaporated at <40° C. in a vacuum, until crystals begin to form and allowed cooling to 5° C. The crystals were filtered and covered with a liberal quantity of ether. The suspension was stirred to insure mixing for a few minutes and filtered under suction as dry as possible.

1.5 g of the above crystals were dissolved in 3 ml of deionized water and 7 ml of concentrated HCl were added. The solution was extracted with ether in a separatory funnel. The lowest layer is transferred to another funnel and 10 ml of $H_2O$ was added. The washing was repeated twice. When the solution turns brown or green in the course of the washing, a few drops of $HNO_3$ were added. The ethereal solution was mixed with 5 ml of deionized water and dried at less than 40° C. in vacuum. An orange solid of the composition $H_6P_2Mo_{18}O_{62}$ was obtained.

TABLE 2

| Example | Heteropoly Acid(HPA) | HPA amount (mg) | Conversion of CHEN (%) | Selectivity for AN (%) |
|---|---|---|---|---|
| 10 | $H_3PMo_6W_6O_{40} \cdot nH_2O$ | 17.3 | 52 | 89 |
| 11 | " | 17.3 | 69 | 88 |
| 12 | " | 52.1 | 86 | 94 |
| 13 | " | 103.8 | 90 | 94 |
| 14 | " | 52.1 | 49 | 92 |
| 15 | " | 104.5 | 59 | 93 |
| 16 | " | 259.3 | 73 | 95 |

| Example | Heteropoly Acid | HPA amount (mg) | Conversion of CHEN (%) | Selectivity for AN (%) |
|---|---|---|---|---|
| 17 | $H_3PMo_{12}O_{40} \cdot nH_2O$ | 13.7 | 50 | 85 |
| 18 | " | 40.6 | 83 | 92 |
| 19 | $H_4SiMo_8W_4O_{40} \cdot nH_2O$ | 15.6 | 61 | 92 |
| 20 | " | 47.8 | 92 | 95 |
| 21 | $H_3PMo_{12}O_{40} \cdot nH_2O$ | 15.5 | 53 | 87 |
| 22 | $H_3PMo_{11}WO_{40} \cdot nH_2O$ | 16 | 56 | 89 |
| 23 | $H_3PMo_{10}W_2O_{40} \cdot nH_2O$ | 14.6 | 57 | 90 |
| 24 | $H_3PMo_4W_8O_{40} \cdot nH_2O$ | 18.5 | 52 | 89 |
| 25 | $H_4SiMo_{12}O_{40} \cdot nH_2O$ | 15.4 | 46 | 89 |
| 26 | $H_4SiMo_{11}WO_{40} \cdot nH_2O$ | 15.9 | 60 | 91 |
| 27 | $H_4SiMo_{10}W_2O_{40} \cdot nH_2O$ | 16.2 | 68 | 92 |
| 28 | $H_4SiMo_6W_6O_{40} \cdot nH_2O$ | 17.5 | 47 | 91 |
| 29 | $H_4PVMo_{11}O_{40} \cdot nH_2O$ | 12.5 | 48 | 85 |
| 30 | $H_6PV_3Mo_9O_{40} \cdot nH_2O$ | 12.1 | 56 | 85 |
| 31 | $H_7PV_4Mo_8O_{40} \cdot nH_2O$ | 12.5 | 61 | 85 |
| 32 | $H_7PV_4W_8O_{40} \cdot nH_2O$ | 17.4 | 60 | 85 |
| 33 | $H_6P_2Mo_{18}O_{62} \cdot nH_2O$ | 20 | 73 | 94 |
| 34 | $H_3PMo_6W_6O_{40} \cdot nH_2O$ | 59 | 69 | 96 |

What is claimed is:

1. A method for producing a ketone compound, which comprises reacting an olefin compound with molecular oxygen and water in the presence of an effective amount of proton and a catalyst comprising
   i) a chlorine-free palladium source, ii) a heteropoly acid or an acid salt of a heteropoly acid, and iii) a mesoporous silicate.

2. A method according to claim 1, wherein the reaction is conducted in the presence of a polar organic solvent.

3. A method according to claim 1, wherein the polar organic solvent is acetonitrile.

4. A method according to claim 1, wherein the proton is provided by a protonic acid which is sulfuric acid or an organic sulfonic acid.

5. A method according to claim 4, wherein the organic sulfonic acid is p-toluenesulfonic acid.

6. A method according to claim 1, wherein the olefin compound is cyclohexene and the ketone compound is cyclohexanone.

7. A method according to claim 1, wherein the polar organic solvent is an alcohol.

* * * * *